United States Patent [19]

Pews

[11] 4,379,930

[45] Apr. 12, 1983

[54] PREPARATION OF 2-T-BUTYL-5-HYDROXYPYRIMIDINE

[75] Inventor: Richard G. Pews, Midland, Mich.

[73] Assignee: The Dow Chemical Company, Midland, Mich.

[21] Appl. No.: 301,686

[22] Filed: Sep. 14, 1981

[51] Int. Cl.$^3$ ............................................. C07D 239/36
[52] U.S. Cl. .................................... 544/298; 544/242
[58] Field of Search ........................................ 544/298

[56] References Cited

U.S. PATENT DOCUMENTS 3,907,797  9/1975  Bodesinsky et al. ................. 544/298

Primary Examiner—Paul M. Coughlan, Jr.

[57] ABSTRACT

The hydrolysis of 2-t-butyl-5-halopyrimidines is carried out in the presence of an alkali metal methoxide and a catalytic amount of an N-oxide, a disulfide or elemental sulfur to prepare 2-t-butyl-5-hydroxypyrimidine in good yields and purity.

4 Claims, No Drawings

PREPARATION OF 2-T-BUTYL-5-HYDROXYPYRIMIDINE

BACKGROUND OF THE INVENTION

In "The Pyrimidines", Interscience (1962), pages 203–204, it is stated that, "The conversion of an active halogeno into an hydroxy group is rather uncommon, and not always easy". In Supplement I of "The Pyrimidines", Interscience (1970), page 148, there is the statement, "The direct hydrolysis of a chloro- to an hydroxy-pyrimidine was avoided for many years, but no such inhibition seems to be operating now. Acid or alkali may be used, although the latter is more usual, . . . " However, attempts to hydrolyze 2-t-butyl-5-bromopyrimidine with sodium methoxide gave considerable quantities of byproduct 2-t-butylpyrimidine.

SUMMARY OF THE INVENTION

I have now found that the hydrolysis of 2-t-butyl-5-halopyrimidines to prepare 2-t-butyl-5-hydroxypyrimidine in good yields and purity may be carried out in the presence of an alkali metal methoxide and a catalytic amount of an N-oxide, a disulfide or elemental sulfur.

DETAILED DESCRIPTION OF THE INVENTION

The reaction is advantageously carried out at temperatures of from 100° to 300° C., preferably 150° to 220° C. and most advantageously at 160° to 180° C. at ambient pressure in a Parr bomb, in the presence of from 0.5 to 20 mole percent of catalyst. The preferred catalyst is elemental sulfur and it is preferably employed in an amount of from 2.5 to 7.5 mole percent. Sodium methoxide is preferably employed, although other alkali metal methoxides such as potassium methoxide may be employed, if desired.

The hydrolysis is advantageously and preferably carried out in a methyl alcohol solvent.

The invention is further illustrated by the following Examples, wherein 2-t-butyl-5-bromopyrimidine was hydrolyzed in the presence of sodium methoxide in excess methanol in a Parr bomb. The following products were obtained:
A. 2-t-butylpyrimidine
B. 2-t-butyl-5-methoxypyrimidine
C. 2-t-butyl-5-hydroxypyrimidine

| Run | Catalyst | Mole % | Temp. °C. | Products A | B | C |
|---|---|---|---|---|---|---|
| 1 | None | 0 | 150 | 23 | 11 | 77 |
| 2 | None | 0 | 150 | 37 | 11 | 58 |
| 3 | 2-Picoline-n-oxide | 10 | 152 | 12 | 12 | 69 |
| 4 | 2-Picoline-n-oxide | 20 | 152 | 12 | 1 | 76 |
| 5 | Di-n-butyl-disulfide | 5 | 160 | 12 | 1 | 91 |
| 6 | Di-n-butyl-disulfide | 10 | 160 | 7 | 1 | 105 |
| 7 | S° | 5 | 163 | 4 | 12 | 88 |
| 8 | S° | 5 | 165 | 5 | 1 | 94 |
| 9 | S° | 2.5 | 153 | 7 | 15 | 80 |
| 10 | S° | 7.5 | 156 | 4 | — | 100 |
| 11 | S° | 5 | 155 | 8 | 4 | 93 |
| 12 | S° | 2.5 | 155 | 7 | 2 | 93 |
| 13 | S° | 1.5 | 160 | 10.14 | — | 101.41 |
| 14 | S° | 0.5 | 160 | 12.06 | — | 97.55 |
| 15* | S° | 2.5 | 170 | 4 | — | 100 |

*Hydrolysis of 2-t-butyl-5-chloropyrimidine.

Various modifications may be made in the present invention without departing from the spirit or scope thereof and it is understood that I limit myself only as defined in the appended claims.

I claim:
1. A method of making 2-t-butyl-5-hydroxypyrimidine which comprises hydrolyzing a 2-t-butyl-5-halopyrimidine in the presence of an alkali metal methoxide and a catalyst comprising 2-picoline-n-oxide, di-n-butyldisulfide or elemental sulfur.
2. Method of claim 1 wherein the halopyrimidine is 2-t-butyl-5-bromopyrimidine.
3. Method of claim 1 wherein the halopyrimidine is 2-t-butyl-5-chloropyrimidine.
4. Method of claim 2 wherein the reaction is carried out at 150° to 220° C.

* * * * *